United States Patent [19]
Linker et al.

[11] Patent Number: 6,025,498
[45] Date of Patent: *Feb. 15, 2000

[54] 4-THIOCARBAMOYL-1-(3-PYRAZOLYL)-PYRAZOLES AND THEIR USE AS HERBICIDES

[75] Inventors: Karl-Heinz Linker; Kurt Findeisen, both of Leverkusen; Wilhelm Haas, Pulheim; Markus Dollinger, Leverkusen, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/029,419

[22] PCT Filed: Aug. 22, 1996

[86] PCT No.: PCT/EP96/03692

§ 371 Date: Feb. 26, 1998

§ 102(e) Date: Feb. 26, 1998

[87] PCT Pub. No.: WO97/09313

PCT Pub. Date: Mar. 13, 1997

[30] Foreign Application Priority Data

Sep. 4, 1995 [DE] Germany ............ 195 32 347

[51] Int. Cl.$^7$ ............ A01N 43/56; C07D 231/38
[52] U.S. Cl. ............ 548/365.4; 504/282
[58] Field of Search ............ 548/365.4; 504/282

[56] References Cited

U.S. PATENT DOCUMENTS 5,756,424  5/1998  Dorfmeister ............ 504/246

FOREIGN PATENT DOCUMENTS 0 542 388 A1  5/1993  European Pat. Off. .
WO94/08999  4/1994  WIPO .

*Primary Examiner*—Robert W. Ramsuer
*Attorney, Agent, or Firm*—Sprung Kramer Schaefer & Briscoe

[57] ABSTRACT

The invention relates to a novel 4-thiocarbamoyl-1-(3-pyrazolyl)-pyrazoles of the general formula (I)

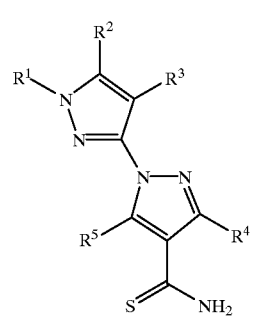

(I)

in which $R^1$, $R^2$, $R^3$, $R^4$ and $R^5$ are each as defined in the description, to a process for their preparation and to their use as herbicides.

6 Claims, No Drawings

4-THIOCARBAMOYL-1-(3-PYRAZOLYL)-PYRAZOLES AND THEIR USE AS HERBICIDES

This application is a 371 of PCT/EP 96/03692 filed Aug. 22, 1996.

The invention relates to novel 4-thiocarbamoyl-1-(3-pyrazolyl)-pyrazoles, to a process for their preparation and to their use as herbicides.

Substituted pyrazolylpyrazoles are already known as potential herbicides (cf. EP 542388, WO 9408999). However, these compounds have not achieved any particular importance.

This invention, accordingly, provides the novel 4-thiocarbamoyl-1-(3-pyrazolyl)-pyrazoles of the general formula (I)

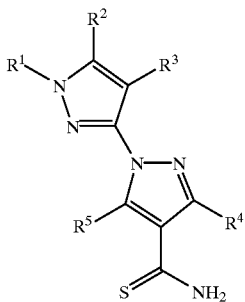

(I)

in which
$R^1$ represents optionally substituted alkyl,
$R^2$ represents a respectively optionally substituted radical from the group consisting of alkyl, alkoxy and alkylthio, or together with $R^1$ represents the grouping —$(CH_2)_m$—X—,
$R^3$ represents hydrogen or halogen,
$R^4$ represents hydrogen or represents optionally substituted alkyl,
$R^5$ represents hydrogen, cyano, nitro, thiocarbamoyl or halogen, represents optionally substituted alkyl, represents optionally substituted aryl, represents the grouping —O—$R^6$, the grouping —$S(O)_n$—$R^7$, the grouping —$NR^8R^9$ or the grouping —$NR^{10}$—CY—$R^{11}$,
$R^6$ represents hydrogen or represents respectively optionally substituted alkyl, alkenyl or alkinyl,
$R^7$ represents a respectively optionally substituted radical from the group consisting of alkyl, alkenyl and alkinyl,
$R^8$ represents hydrogen or represents a respectively optionally substituted radical from the group consisting of alkyl, alkenyl, alkinyl, cycloalkyl, cycloalkylalkyl, aryl and arylalkyl,
$R^9$ represents hydrogen or represents a respectively optionally substituted radical from the group consisting of alkyl, alkoxy, alkenyl, alkinyl, cycloalkyl, cycloalkylalkyl, aryl and aralkyl or represents the grouping —$S(O)$—$R^7$, or together with $R^8$ represents alkanediyl,
$R^{10}$ represents hydrogen or represents a respectively optionally substituted radical from the group consisting of alkyl, alkenyl and alkinyl,
$R^{11}$ represents hydrogen, represents optionally substituted alkyl or represents optionally substituted aryl,
m represents the numbers 2 or 3,
n represents the numbers 0, 1 or 2,
x represents $CH_2$, O, S, $S(O)_n$, NH or $NCH_3$, and
Y represents O or S.

The novel 4-thiocarbamoyl-1-(3-pyrazolyl)-pyrazoles of the general formula (I) are obtained when 4-cyano-1-(3-pyrazolyl)-pyrazoles of the general formula (II)

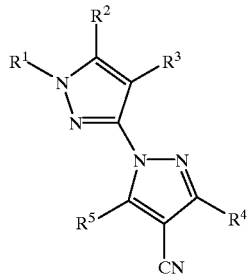

(II)

in which
$R^1$, $R^2$, $R^3$, $R^4$ and $R^5$ are each as defined above,
are reacted with hydrogen sulphide, thioacetic acid or thioacetamide, if appropriate in the presence of a reaction auxiliary and if appropriate in the presence of a diluent.

The novel 4-thiocarbamoyl-1-(3-pyrazolyl)-pyrazoles of the general formula (I) have strong herbicidal activity.

In the definitions, the saturated or unsaturated hydrocarbon chains such as alkyl, alkanediyl, alkenyl or alkinyl, are each, even in combination with hetero atoms, such as in alkoxy or alkylthio, straight-chain or branched.

Halogen generally represents fluorine, chlorine, bromine or iodine, preferably fluorine, chlorine or bromine, in particular fluorine or chlorine.

The invention preferably provides compounds of the formula (I) in which
$R^1$ represents optionally cyano-, halogen- or $C_1$–$C_4$-alkoxy-substituted alkyl having 1 to 6 carbon atoms,
$R^2$ represents a respectively optionally cyano-, halogen- or $C_1$–$C_4$-alkoxy-substituted radical from the group consisting of alkyl, alkoxy and alkylthio having in each case 1 to 6 carbon atoms, or together with $R^1$ represents the grouping —$(CH_2)_m$—X—,
$R^3$ represents hydrogen or halogen,
$R^4$ represents hydrogen or represents optionally cyano-, halogen- or $C_1$–$C_4$-alkoxy-substituted alkyl having 1 to 6 carbon atoms,
$R^5$ represents hydrogen, cyano, nitro, thiocarbamoyl or halogen, represents optionally cyano-, halogen- or $C_1$–$C_4$-alkoxy-substituted alkyl having 1 to 6 carbon atoms, represents optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, represents the grouping —O—$R^6$, the grouping —$S(O)_n$—$R^7$, the grouping —$NR^8R^9$ or the grouping —$NR^{10}$—CY—$R^{11}$,
$R^6$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, or represents respectively optionally cyano-, halogen- or $C_1$–$C_4$-alkoxycarbonyl-substituted alkenyl or alkinyl having in each case 2 to 6 carbon atoms,
$R^7$ represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, or represents respectively optionally cyano-, halogen- or $C_1$–$C_4$-alkoxycarbonyl-substituted alkenyl or alkinyl having in each case 2 to 6 carbon atoms,
$R^8$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, represents respectively optionally cyano-, halogen- or $C_1$–$C_4$-alkoxycarbonyl-substituted alkenyl or alkinyl having in each case 2 to 6 carbon atoms, represents respectively optionally cyano-, halogen- or $C_1$–$C_4$-alkyl-substituted cycloalkyl or cycloalkylalkyl having in each case 3 to 6 carbon atoms in the cycloalkyl moieties and optionally 1 to 4 carbon atoms in the alkyl moieties, or represents respectively optionally cyano-, thiocarbamoyl-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_4$-alkyl, $R^9$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, represents respectively optionally cyano-, halogen- or $C_1$–$C_4$-alkoxycarbonyl-substituted alkenyl or alkinyl having in each case 2 to 6 carbon atoms, represents optionally cyano-, halogen- or $C_1$–$C_4$-alkoxy-substituted alkoxy having 1 to 6 carbon atoms, represents the grouping —S(O)$_n$—$R^7$, represents respectively optionally cyano-, halogen- or $C_1$–$C_4$-alkyl-substituted cycloalkyl or cycloalkylalkyl having in each case 3 to 6 carbon atoms in the cycloalkyl moieties and optionally 1 to 4 carbon atoms in the alkyl moieties, or represents respectively optionally cyano-, thiocarbamoyl-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_4$-alkyl, or together with $R^8$ represents alkanediyl having 2 to 6 carbon atoms, $R^{10}$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, or represents respectively optionally cyano-, halogen-, or $C_1$–$C_4$-alkoxycarbonyl-substituted alkenyl or alkinyl having in each case 2 to 6 carbon atoms, $R^{11}$ represents hydrogen, represents optionally cyano-, halogen- or $C_1$–$C_4$-alkoxy-substituted alkyl having 1 to 6 carbon atoms, $C_1$–$C_4$-halogenoalkyl, $C_1$–$C_4$-alkoxy or $C_1$–$C_4$-halogenoalkoxy or represents optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy- substituted phenyl, m represents the numbers 2 or 3, n represents the numbers 0, 1 or 2, x represents $CH_2$, O, S, S(O)$_n$, NH or $NCH_3$, and Y represents O or S.

The invention in particular provides compounds of the formula (I) in which $R^1$ represents respectively optionally cyano-, fluorine-, chlorine-, methoxy- or ethoxy-substituted methyl, ethyl, n- or i-propyl, n-, i-, s- or t-butyl, $R^2$ represents respectively optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, or together with $R^1$ represents the grouping —(CH$_2$)$_m$—X—, $R^3$ represents hydrogen, fluorine, chlorine or bromine, $R^4$ represents hydrogen or represents respectively optionally cyano-, fluorine-, chlorine-, methoxy- or ethoxy-substituted methyl, ethyl, n- or i-propyl, n-, i-, s- or t-butyl, $R^5$ represents hydrogen, cyano, nitro, thiocarbamoyl, fluorine, chorine or bromine, represents respectively optionally cyano-, fluorine-, chlorine-, methoxy- or ethoxy-substituted methyl, ethyl, n- or i-propyl, n-, i-, s- or t-butyl, represents optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, represents the grouping —O—$R^6$, the grouping —S(O)$_n$—$R^7$, the grouping —NR$^8$R$^9$ or the grouping —NR$^{10}$—CY—R$^{11}$, $R^6$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, or represents respectively optionally cyano-, fluorine-, chlorine-, bromine-, methoxycarbonyl- or ethoxycarbonyl-substituted propenyl, butenyl, propinyl or butinyl, $R^7$ represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, or represents respectively optionally cyano-, fluorine-, chlorine-, bromine-, methoxycarbonyl- or ethoxycarbonyl-substituted propenyl, butenyl, propinyl or butinyl, $R^8$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, represents respectively optionally cyano-, fluorine-, chlorine-, bromine-, methoxycarbonyl- or ethoxycarbonyl-substituted propenyl, butenyl, propinyl or butinyl, represents respectively optionally cyano-, fluorine-, chlorine-, methyl-, or ethyl-substituted cyclopropyl, cyclobutyl, cyclopentyl, cyclohexyl, cyclopropylmethyl, cyclobutylmethyl, cyclopentylmethyl or cyclohexylmethyl, or represents respectively optionally cyano-, thiocarbamoyl-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl or benzyl, $R^9$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, represents respectively optionally cyano-, fluorine-, chlorine-, bromine-, methoxycarbonyl- or ethoxycarbonyl-substituted propenyl, butenyl, propinyl or butinyl, represents optionally cyano-, fluorine-, chlorine-, methoxy- or ethoxy-substituted methoxy, ethoxy, n- or i-propoxy, n-, i-, s- or t-butoxy, represents the grouping —S(O)$_n$—$R^7$, represents respectively optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents respectively optionally cyano-, thiocarbamoyl-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl or benzyl, or together with $R^8$ represents propane-1,3-diyl (trimethylene) or butane-1,4-diyl (tetramethylene), $R^{10}$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, or represents respectively optionally cyano-, fluorine-, chlorine-, bromine-, methoxycarbonyl- or ethoxycarbonyl-substituted propenyl, butenyl, propinyl or butinyl, $R^{11}$ represents hydrogen, represents respectively optionally cyano-, fluorine-, chlorine-, methoxy- or ethoxy-substituted methyl, ethyl, n- or i-propyl, n-, i-, s- or t-butyl, or represents optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, m represents the numbers 2 or 3,
n represents the numbers 0, 1 or 2,
x represents $CH_2$, O, $S(O)_n$, NH or $NCH_3$, and
Y represents O or S.

The radical definitions listed above, whether generally or in the ranges of preference, apply not only to the end products of the formula (I) but also, correspondingly, to the starting materials and/or intermediates required in each case for the preparation. These radical definitions can be combined with one another as desired, thus including combinations between the preferred ranges indicated.

Examples of the compounds of the formula (I) according to the invention are listed in the groups below:

(IA-1)

Group 1

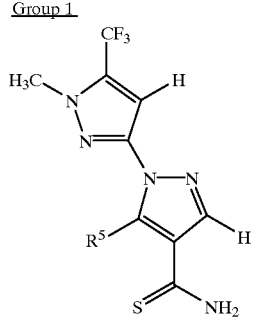

$R^5$ has, for example, the meanings listed below:

$CH_3$, $C_2H_5$, $CF_3$, $C_2F_5$, $CH(CH_3)_2$, $CH_2CH_2CH_3$, $C(CH_3)_3$, $CH_2OCH_3$, $CH_2CH_2OCH_3$, Cl, Br, F, CN, $CSNH_2$, Ph, $NO_2$, $NH_2$, $NHCH_3$, $NHC_2H_5$, $NHCH(CH_3)_2$, $NHCH_2CH_2CH_3$, $NHCH_2CH=CH_2$, $NHCH_2C\equiv CH$, $NHCH(CH_3)C\equiv CH$, $NHCH_2CH_2OCH_3$, $NHSO_2CH_3$ $NHSO_2C_2H_5$, $NHSO_2CH(CH_3)_2$, $NHSO_2CH_2CH_2CH_3$, $NHCH_2Ph$, $NHCH_2CH_2N(CH_3)_2$, $N(CH_3)_2$, $N(CH_3)C_2H_5$, $N(CH_3)CH(CH_3)_2$, $N(CH_3)CH(CH_3)CH_2OCH_3$, $N(CH_3)CH_2CH_2N(CH_3)_2$, $N(CH_3)SO_2CH_3$, $N(CH_3)SO_2C_2H_5$, $N(CH_3)CH_2CH=CH_2$, $N(CH_3)CH_2C\equiv CH$,

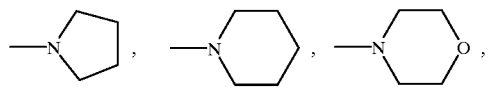

$NHCOCH_3$, $NHCOCF_3$, NHCO-cyclopropyl, $NHCO(CH_2)_2Cl$, NHCOPh, $N(COCH_3)_2$, $N(CH_3)COCF_3$, $N(CH_2CH=CH_2)COCF_3$, $N(CH_2C\equiv CH)COCF_3$, $N(CH_3)COCH_2Cl$, $N(CH_3)CO$-cyclopropyl, $OCH_3$, $OC_2H_5$, $OCH_2CH_2CH_3$, $OCH(CH_3)_2$, $OCH_2CH_2CH=CH_3$, $OCH_2CH=CH_2$, $OCH_2C\equiv CH$, $OCH_2COOC_2H_5$, $OCH(CH_3)COOC_2H_5$, $OCH(CH_3)C\equiv CH$, $SCH_3$, $SOCH_3$, $SO_2CH_3$, $SC_2H_5$, $SCH(CH_3)_2$, $SCH_2COOC_2H_5$, $SCH(CH_3)COOC_2H_5$, $SCH_2CH=CH_2$, $SCH_2C\equiv CH$.

(IA-2)

Group 2

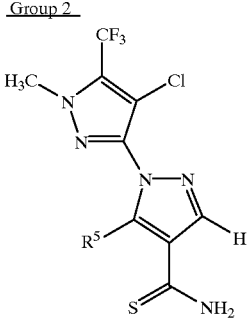

$R^5$ has, for example, the meanings listed above under Group 1:

(IA-3)

Group 3

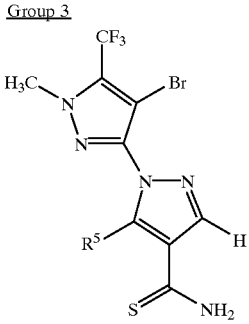

$R^5$ has, for example, the meanings listed above under Group 1:

(IA-4)

Group 4

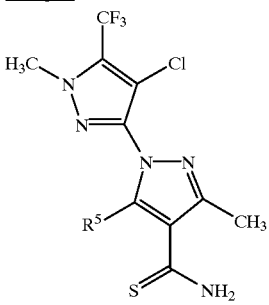

$R^5$ has, for example, the meanings listed above under Group 1:

Group 5

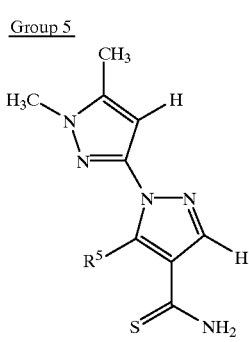

(IA-5)

R⁵ has, for example, the meanings listed above under Group 1:

Group 6

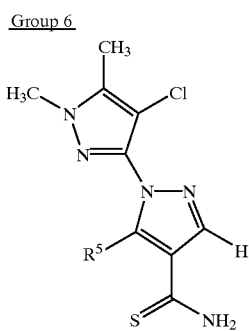

(IA-6)

R⁵ has, for example, the meanings listed above under Group 1:

Group 7

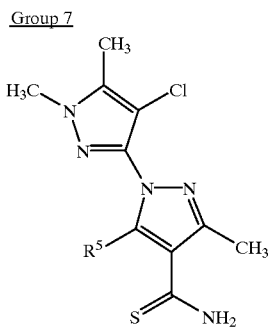

(IA-7)

R⁵ has, for example, the meanings listed above under Group 1:

Group 8

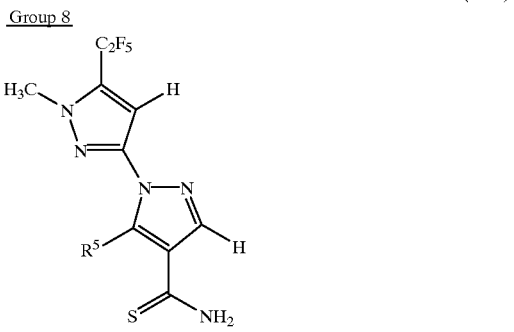

(IA-8)

R⁵ has, for example, the meanings listed above under Group 1:

Group 9

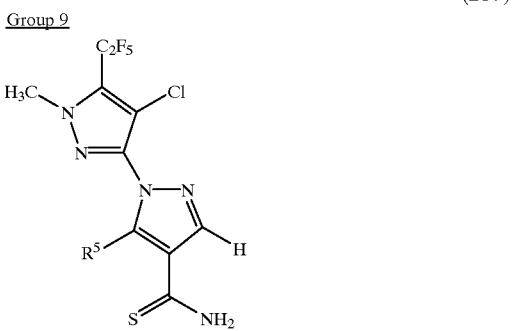

(IA-9)

R⁵ has, for example, the meanings listed above under Group 1:

Group 10

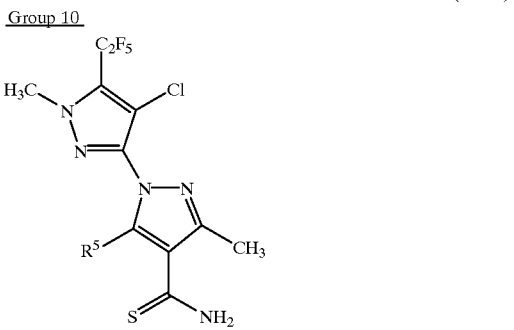

(IA-10)

R⁵ has, for example, the meanings listed above under Group 1:

Group 11 (IA-11)

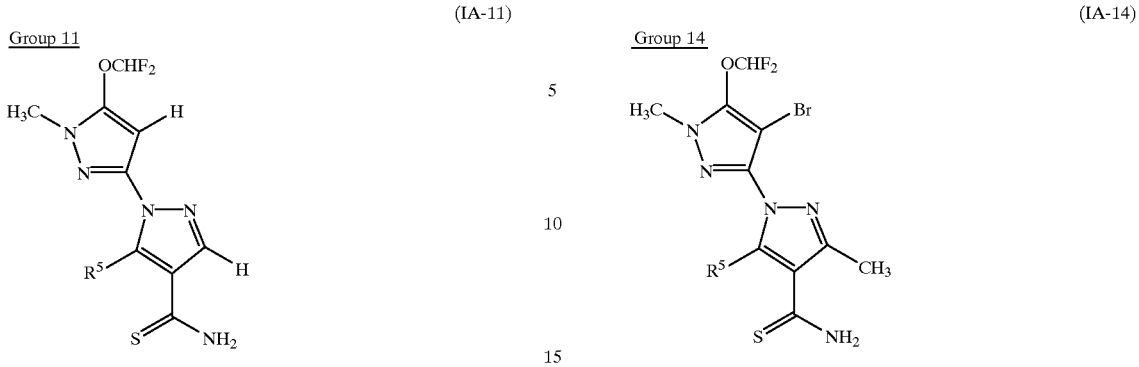

R⁵ has, for example, the meanings listed above under Group 1:

Group 12 (IA-12)

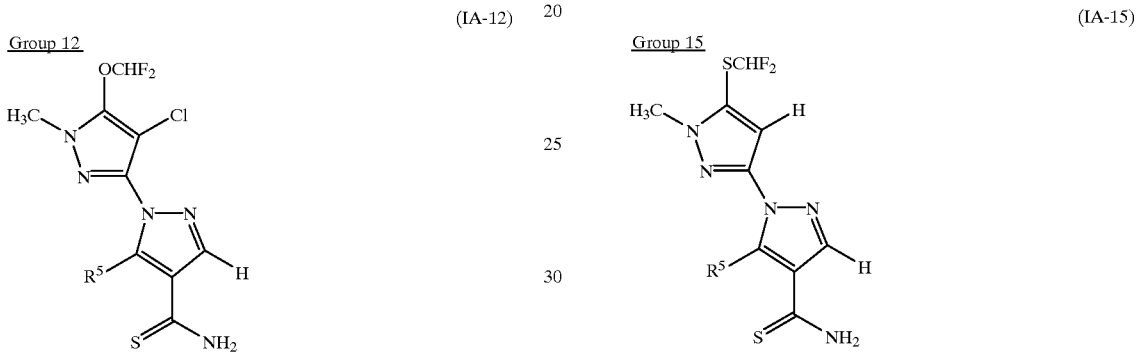

R⁵ has, for example, the meanings listed above under Group 1:

Group 13 (IA-13)

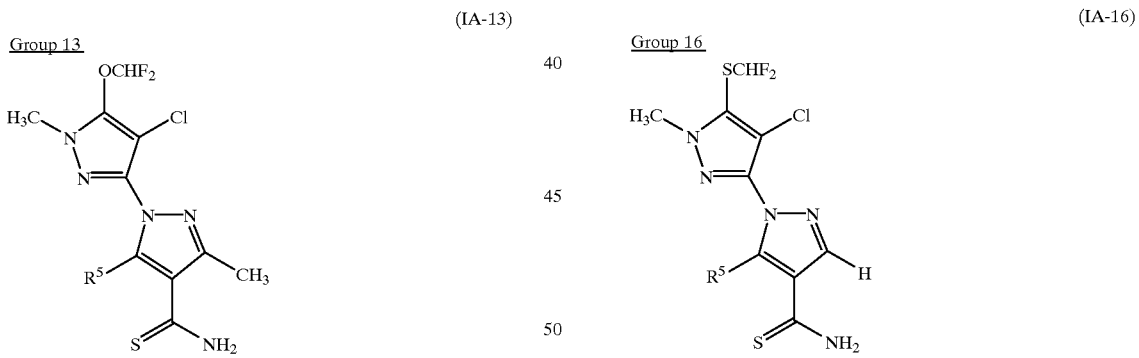

R⁵ has, for example, the meanings listed above under Group 1:

Group 14 (IA-14)

R⁵ has, for example, the meanings listed above under Group 1:

Group 15 (IA-15)

R⁵ has, for example, the meanings listed above under Group 1:

Group 16 (IA-16)

R⁵ has, for example, the meanings listed above under Group 1:

Group 17

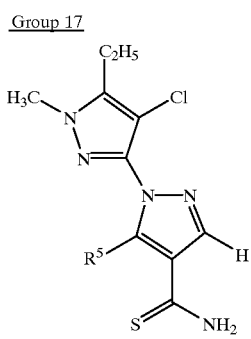
(IA-17)

R⁵ has, for example, the meanings listed above under Group 1:

Group 18

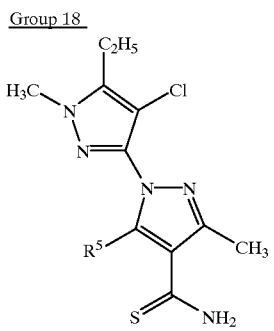
(IA-18)

R⁵ has, for example, the meanings listed above under Group 1:

Group 19

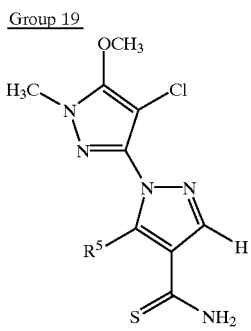
(IA-19)

R⁵ has, for example, the meanings listed above under Group 1:

Group 20

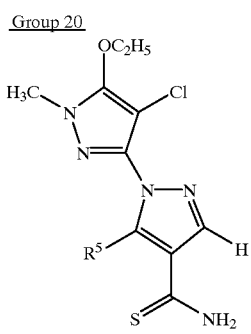
(IA-20)

R⁵ has, for example, the meanings listed above under Group 1:

Group 21

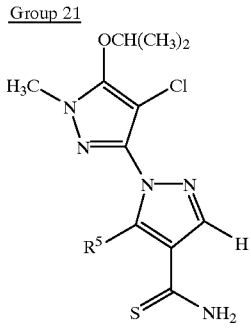
(IA-21)

R⁵ has, for example, the meanings listed above under Group 1:

Group 22

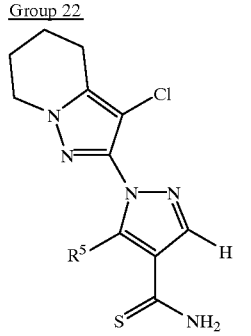
(IA-22)

R⁵ has, for example, the meanings listed above under Group 1:

Group 23 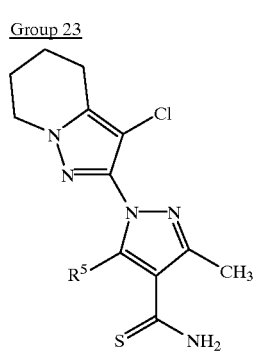 (IA-23)

$R^5$ has, for example, the meanings listed above under Group 1:

Group 24 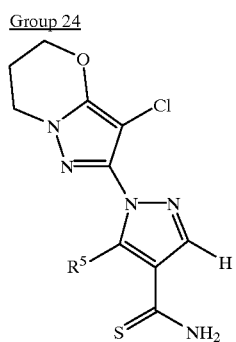 (IA-24)

$R^5$ has, for example, the meanings listed above under Group 1:

Group 25 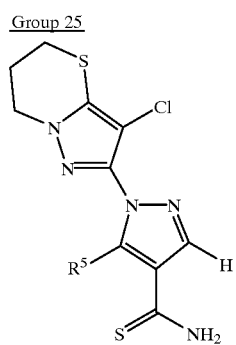 (IA-25)

$R^5$ has, for example, the meanings listed above under Group 1:

Group 26 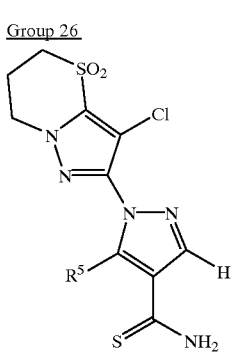 (IA-26)

$R^5$ has, for example, the meanings listed above under Group 1:

Group 27 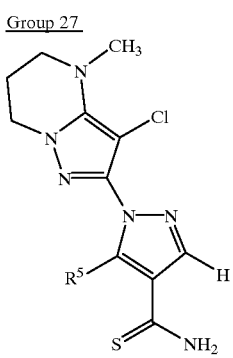 (IA-27)

$R^5$ has, for example, the meanings listed above under Group 1:

Using, for example, 5-amino-4-cyano-3-chloro-1-(1-methyl-5-trifluoromethyl-3-pyrazolyl)-pyrazole and hydrogen sulphide as starting materials, the course of the reaction in the process according to the invention can be illustrated by the following equation:

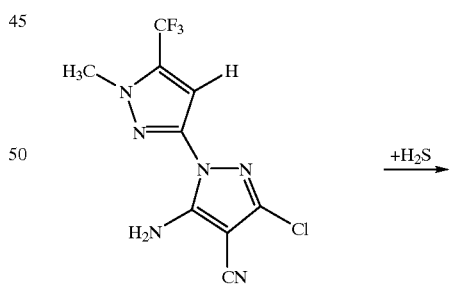

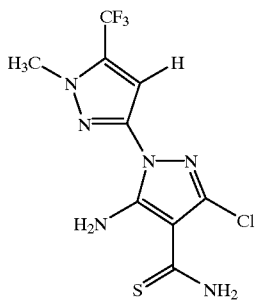

A general definition of the 4-cyano-1-(3-pyrazolyl)-pyrazoles to be used as starting materials in the process according to the invention for preparing compounds of the formula (I) is given by the formula (II). In formula (II), $R^1$, $R^2$, $R^3$, $R^4$ and $R^5$ each preferably or in particular have those meanings which have already been indicated above, in connection with the description of the compounds of the formula (I), to be prepared according to the invention, as being preferable or particularly preferable for $R^1$, $R^2$, $R^3$, $R^4$ and $R^5$.

The starting materials of the formula (II) are known and/or can be prepared by processes known per se (cf. EP 542388, WO 9408999).

The process according to the invention for preparing compounds of the formula (1) is, if appropriate, carried out in the presence of a diluent. Suitable diluents are generally the conventional organic solvents. These preferably include aliphatic, alicyclic and aromatic, optionally halogenated hydrocarbons, such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or carbon tetrachloride, dialkyl ethers, such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones, such as, for example, acetone, butanone, (methyl ethyl ketone), methyl i-propyl ketone or methyl i-butyl ketone, nitriles, such as, for example, acetonitrile, propionitrile, butyronitrile or benzonitrile; amides, such as, for example, N,N-dimethyl-formamide (DMF), N,N-dimethyl-acetamide, N-methyl-formanilide, N-methyl-pyrrolidone or hexamethylphosphoric triamide; esters, such as, for example, methyl acetate, ethyl acetate, n- or i-propyl acetate, n-, i- or s-butyl acetate; sulphoxides, such as, for example, dimethyl sulphoxide; alkanols, such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; mixtures thereof with water or pure water.

The process according to the invention for preparing compounds of the formula (I) is preferably carried out in the presence of a suitable reaction auxiliary. Suitable reaction auxiliaries are generally the conventional inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), and 1,8-diazabicyclo[5,4,0]-undec-7-ene (DBU).

The reaction temperatures in the practise of the process according to the invention can be varied within a relatively wide range. The reactions are in general carried out at temperatures between 0° C. and 120° C., preferably between 10° C. and 100° C.

The process according to the invention is generally carried out at atmospheric pressure. However, it is also possible to carry out the process according to the invention under elevated or reduced pressure—generally between 0.1 bar and 10 bar.

In the practise of the process according to the invention, the starting materials of the formula (II) are generally precharged in a suitable diluent in the presence of a reaction auxiliary, and the hydrogen sulphide or the thioacetic acid or the thioacetamide is slowly metered in. The reaction mixture is stirred at the temperature required in each case until the reaction has ended. Work-up in the process according to the invention is in each case carried out by conventional methods (cf. the preparation examples).

The active compounds according to the invention can be used as defoliants, desiccants, haulm killers and, especially, as weed-killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, lpomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotvledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual cultures.

The compounds of the formula (I) according to the invention are suitable, in particular, for the selective control of monocotyledonous and dicotyledonous weeds in monocotyledonous and dicotyledonous cultures, both pre-emergence and post-emergence.

To a certain extent, the compounds of the formula (I) also have insecticide action.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonylureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; and others, such as aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

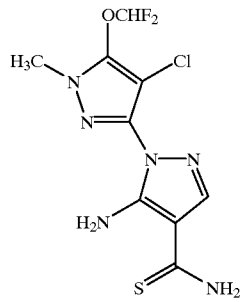

2.9 g (10 mmol) of 5-amino-4-cyano-1-(4-chloro-5-difluoromethoxy-1-methyl-3-pyrazolyl)-pyrazole are precharged with 20 ml of pyridine and 10 ml of triethylamine and heated to 70° C. while hydrogen sulphide is passed through the mixture. Hydrogen sulphide is continued to be passed through the solution for 2 hours at 70° C., and the mixture is then flushed with nitrogen, cooled and concentrated using water pump vacuum. The residue is stirred with water and acidified with concentrated hydrochloric acid, and the crystalline product is isolated by filtration.

2.7 g (84% of theory) of 5-amino-1-(4-chloro-5-difluoromethoxy-1-methyl-3-pyrazolyl)-4-thiocarbamoyl-pyrazole of melting point 156° C. are obtained.

Example 2

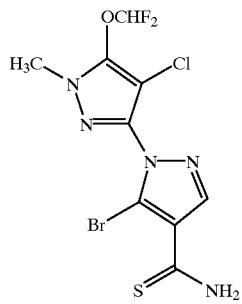

2.5 g (7 mmol) of 5-bromo-4-cyano-1-(4-chloro-5-difluoromethoxy-1-methyl-3-pyrazolyl)-pyrazole and 2.2 g (29 mmol) of thioacetic acid are stirred for 45 minutes at reflux temperature, and the mixture is concentrated under water pump vacuum using a rotary evaporator. The residue is stirred with diethyl ether the crystalline product is isolated by filtration.

2.1 g (78% of theory) of 5-bromo-1-(4-chloro-5-difluoromethoxy-1-methyl-3-pyrazolyl)-4-thiocarbamoyl-pyrazole of melting point 175° C. are obtained.

Using the methods of Examples 1 and 2, further compounds of the formula (1)—cf. Table I—can be prepared:

TABLE 1

Examples of compounds of the formula (I)

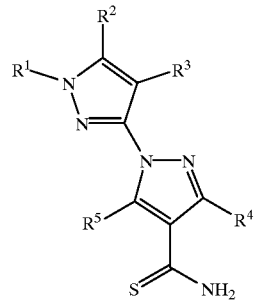

| Ex. No. | $R^1$ | $R^2$ | $R^3$ | $R^4$ | $R^5$ | Melting point (° C.) |
|---|---|---|---|---|---|---|
| 3 | $CH_3$ | $OCHF_2$ | Cl | H | $CH_3$ | 133 |
| 4 | $CH_3$ | $OCHF_2$ | Cl | H | H | 140 |
| 5 | $CH_3$ | $OCHF_2$ | Cl | $CH_3$ | $NH_2$ | 170 |

Use Examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of the active compound. Advantageously, the amount of water per unit area is kept constant. The active compound concentration in the preparation is not important, only the active compound application rate per unit area being decisive.

After three weeks, the degree of damage to the plants is rated in % damage in comparison to the development of the untreated control.

The figures denote:

0%=no action (like untreated control)

100%=total destruction

In this test, a very strong activity against weeds such as Digitaria (80%), Echinochloa (95%), Abutilon (100%), Amaranthus (100%) and Chenopodium (100%) is shown, for example, by the compound of Preparation Example 1 at an application rate of 125 g/ha, combined with good tolerance by crops, such as, for example, barley and cotton (0–10%).

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no action (like untreated control)

100%=total destruction

In this test, a very strong activity against weeds such as Echinochloa (100%), Setaria (95%), Abutilon (100%), Amaranthus (100%) and Chenopodium (100%) is shown, for example, by the compound of Preparation Example 1 at an application rate of 250 g/ha, combined with good tolerance by crops, such as, for example, wheat (10%).

We claim:

1. 4Thiocarbamoyl-1-(3-pyrazolyl)-pyrazoles of the general formula (I)

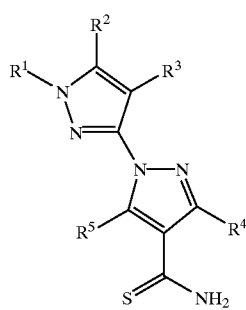

(I)

in which
- $R^1$ represents optionally substituted alkyl,
- $R^2$ represents a respectively optionally substituted radical from the group consisting of alkyl, alkoxy and alkylthio, or together with $R^1$ represents the grouping —$(CH_2)_m$—X—,
- $R^3$ represents hydrogen or halogen,
- $R^4$ represents hydrogen or represents optionally substituted alkyl,
- $R^5$ represents hydrogen, cyano, nitro, thiocarbamoyl or halogen, represents optionally substituted alkyl, represents optionally substituted aryl, represents the grouping —O—$R^6$, the grouping —$S(O)_n$—$R^7$, the grouping —$NR^8R^9$ or the —$NR^{10}$—CY—$R^{11}$,
- $R^6$ represents hydrogen or represents respectively optionally substituted alkyl, alkenyl or alkinyl,
- $R^7$ represents a respectively optionally substituted radical from the group consisting of alky, alkenyl and alkinyl,
- $R^8$ represents hydrogen or represents a respectively optionally substituted radical from the group consisting of alkyl, alkenyl, alkinyl, cycloalkyl, cycloalkylalkyl, aryl and arylalkyl,
- $R^9$ represents hydrogen or represents a respectively optionally substituted radical from the group consisting of alkyl, alkoxy, alkenyl, alkinyl, cycloalkyl, cycloalkylalkyl, aryl and aralkyl or represents the grouping —$S(O)_n$—$R^7$, or together with $R^8$ represents alkanediyl,
- $R^{10}$ represents hydrogen or represents a respectively optionally substituted radical from the group consisting of alkyl, alkenyl and alkinyl,
- $R^{11}$ represents hydrogen, represents optionally substituted alkyl $C_1$–$C_4$ alkoxy or $C_1$–$C_4$ halogenoalkoxy or represents optionally substituted aryl,
- m represents the numbers 2 or 3,
- n represents the numbers 0, 1 or 2,
- x represents $CH_2$, O, S, $S(O)_n$, NH or $NCH_3$, and
- Y represents O or S.

2. Process for preparing 4-thiocarbamoyl-1-(3-pyrazolyl)-pyrazoles of the general formula (I)

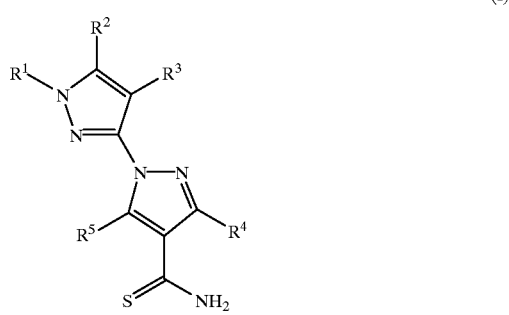

(I)

in which
$R^1$, $R^2$, $R^3$, $R^4$ and $R^5$ are each as defined in claim 1,
characterized in that 4-cyano-1-(3-pyrazolyl)-pyrazoles of the general formula (II)

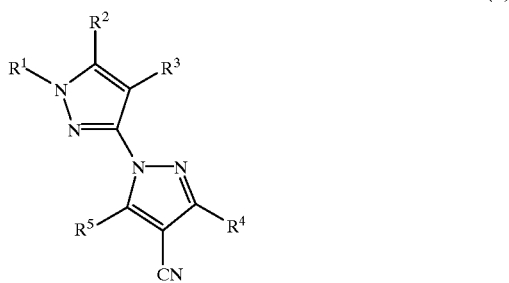

(II)

in which
$R^1$, $R^2$, $R^3$, $R^4$ and $R^5$ are each as defined above,
are reacted with hydrogen sulphide, thioacetic acid or thioacetamide, if appropriate in the presence of a reaction auxiliary and if appropriate in the presence of a diluent.

3. 4-Thiocarbamoyl-1-(3-pyrazolyl)-pyrazoles of the general formula (I) according to claim 1, characterized in that
- $R^1$ represents optionally cyano-, halogen- or $C_1$–$C_4$-alkoxy-substituted alkyl having 1 to 6 carbon atoms,
- $R^2$ represents a respectively optionally cyano-, halogen- or $C_1$–$C_4$-alkoxy-substituted radical from the group consisting of alkyl, alkoxy and alkylthio having in each case 1 to 6 carbon atoms, or together with $R^1$ represents the grouping —$(CH_2)_m$—X—,
- $R^3$ represents hydrogen or halogen,
- $R^4$ represents hydrogen or represents optionally cyano-, halogen- or $C_1$–$C_4$-alkoxy-substituted alkyl having 1 to 6 carbon atoms,
- $R^5$ represents hydrogen, cyano, nitro, thiocarbamoyl or halogen, represents optionally cyano-, halogen- or $C_1$–$C_4$-alkoxy-substituted alkyl having 1 to 6 carbon atoms, represents optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, represents the grouping —O—$R^6$, the grouping —S(O)$_n$—$R^7$, the grouping —$NR^8R^9$ or the grouping —$NR^{10}$—CY—$R^{11}$, $R^6$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, or represents respectively optionally cyano-, halogen- or $C_1$–$C_4$-alkoxycarbonyl-substituted alkenyl or alkinyl having in each case 2 to 6 carbon atoms, $R^7$ represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, or represents respectively optionally cyano-, halogen- or $C_1$–$C_4$-alkoxycarbonyl-substituted alkenyl or alkinyl having in each case 2 to 6 carbon atoms, $R^8$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, represents respectively optionally cyano-, halogen- or $C_1$–$C_4$-alkoxycarbonyl-substituted alkenyl or alkinyl having in each case 2 to 6 carbon atoms, represents respectively optionally cyano-, halogen- or $C_1$–$C_4$-alkyl-substituted cycloalkyl or cycloalkylalkyl having in each case 3 to 6 carbon atoms in the cycloalkyl moieties and optionally 1 to 4 carbon atoms in the alkyl moieties, or represents respectively optionally cyano-, thiocarbamoyl-, nitro-, halogen-, $C_1$–$C_4$-alkyl-, $C_1$–$C_4$-halogeno-alkyl-, $C_1$–$C_4$-alkoxy- or $C_1$–$C_4$-halogenoalkoxy-substituted phenyl or phenyl-$C_1$–$C_4$-alkyl, $R^9$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, represents respectively optionally cyano-, halogen, or $C_1$–$C_4$-alkoxycarbonyl-substituted alkenyl or alkinyl having in each case 2 to 6 carbon atoms, represents optionally cyano-, halogen- or $C_1$–$C_4$-alkoxy-substituted alkoxy having 1 to 6 carbon atoms, represents the grouping —S(O)$_n$—$R^7$, represents respectively optionally cyano-, halogen- or $C_1$–$C_4$-alkyl-substituted cycloalkyl or cycloalkylalkyl having in each case 3 to 6 carbon atoms in the cycloalkyl moieties and optionally 1 to 4 carbon atoms in the alkyl moieties, or represents respectively optionally cyano-, thiocarbamoyl-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_4$-alkyl, or together with $R^8$ represents alkanediyl having 2 to 6 carbon atoms, $R^{10}$ represents hydrogen, represents optionally cyano-, halogen-, $C_1$–$C_4$-alkoxy-, $C_1$–$C_4$-alkyl-carbonyl- or $C_1$–$C_4$-alkoxy-carbonyl-substituted alkyl having 1 to 6 carbon atoms, or represents respectively optionally cyano-, halogen-, or $C_1$–$C_4$-alkoxycarbonyl-substituted alkenyl or alkinyl having in each case 2 to 6 carbon atoms, $R^{11}$ represents hydrogen, represents optionally cyano-, halogen- or $C_1$–$C_4$-alkoxy-substituted alkyl having 1 to 6 carbon atoms, $C_1$–$C_4$-halogenoalkyl, $C_1$–$C_4$-alkoxy or $C_1$–$C_4$-halogenoalkoxy or represents optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy- substituted phenyl, m represents the numbers 2 or 3, n represents the numbers 0, 1 or 2, x represents $CH_2$, O, S, S(O)$_n$, NH or $NCH_3$, and Y represents O or S.

4. 4-Thiocarbamoyl-1-(3-pyrazolyl)-pyrazoles of the general formula (I) according to claim 1, characterized in that $R^1$ represents respectively optionally cyano-, fluorine-, chlorine-, methoxy- or ethoxy-substituted methyl, ethyl, n- or i-propyl, n-, i-, s- or t-butyl, $R^2$ represents respectively optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, or together with $R^1$ represents the grouping —(CH$_2$)$_m$—X—, $R^3$ represents hydrogen, fluorine, chlorine or bromine, $R^4$ represents hydrogen or represents respectively optionally cyano-, fluorine-, chlorine-, methoxy- or ethoxy-substituted methyl, ethyl, n- or i-propyl, n-, i-, s- or t-butyl, $R^5$ represents hydrogen, cyano, nitro, thiocarbamoyl, fluorine, chorine or bromine, represents respectively optionally cyano-, fluorine-, chlorine-, methoxy- or ethoxy-substituted methyl, ethyl, n- or i-propyl, n-, i-, s- or t-butyl, represents optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, represents the grouping —O—$R^6$, the grouping —S(O)$_n$—$R^7$, the grouping —$NR^8R^9$ or the grouping —$NR^{10}$—CY—$R^{11}$, $R^6$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, or represents respectively optionally cyano-, fluorine-, chlorine-, bromine-, methoxycarbonyl- or ethoxycarbonyl-substituted propenyl, butenyl, propinyl or butinyl, $R^7$ represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, or represents respectively optionally cyano-, fluorine-, chlorine-, bromine-, methoxycarbonyl- or ethoxycarbonyl-substituted propenyl, butenyl, propinyl or butinyl, $R^8$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, represents respectively optionally cyano-, fluorine-, chlorine-, bromine-, methoxycarbonyl- or ethoxycarbonyl-substituted propenyl, butenyl, propinyl or butinyl, represents respectively optionally cyano-, fluorine-, chlorine-, methyl-, or ethyl-substituted cyclopropyl, cyclobutyl, cyclopentyl, cyclohexyl, cyclopropylmethyl, cyclobutylmethyl, cyclopentylmethyl or cyclohexylmethyl, or represents respectively optionally cyano-, thiocarbamoyl-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl or benzyl, $R^9$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, represents respectively optionally cyano-, fluorine-, chlorine-, bromine-, methoxycarbonyl- or ethoxycarbonyl-substituted propenyl, butenyl, propinyl or butinyl, represents optionally cyano-, fluorine-, chlorine-, methoxy- or ethoxy-substituted methoxy, ethoxy, n- or i-propoxy, n-, i-, s- or t-butoxy, represents the grouping —S(O)$_n$—R$^7$, represents respectively optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents respectively optionally cyano-, thiocarbamoyl-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl or benzyl, or together with $R^8$ represents propane-1,3-diyl (trimethylene) or butane-1,4-diyl (tetramethylene), $R^{10}$ represents hydrogen, represents respectively optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, or represents respectively optionally cyano-, fluorine-, chlorine-, bromine-, methoxycarbonyl- or ethoxycarbonyl-substituted propenyl, butenyl, propinyl or butinyl, $R^{11}$ represents hydrogen, represents respectively optionally cyano-, fluorine-, chlorine-, methoxy- or ethoxy-substituted methyl, ethyl, n- or i-propyl, n-, i-, s- or t-butyl, or represents optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, m represents the numbers 2 or 3, n represents the numbers 0, 1, or 2, x represents $CH_2$, O, S, $S(O)_n$, NH or $NCH_3$, and Y represents O or S.

5. Herbicidal compositions, characterized by a content of at least one 4-thiocarbamoyl-1-(3-pyrazolyl)-pyrazole of the general formula (I) according to claim 1.

6. A method for controlling undesirable plants, characterized in that 4-thiocarbamoyl-1-(3-pyrazolyl)-pyrazoles of the general formula (I) according to claim 1 are allowed to act on undesirable plants and/or their habitat.

* * * * *